United States Patent [19]

Terasawa et al.

[11] Patent Number: 5,256,551
[45] Date of Patent: Oct. 26, 1993

[54] METHOD OF TREATING MICROORGANISM CELLS CONTAINING TRYPTOPHANASE OR TREATED PRODUCT THEREOF

[75] Inventors: Masato Terasawa; Mitsunobu Shimazu; Fuzio Endo; Hideaki Yukawa, all of Ami, Japan

[73] Assignee: Research Association for Utilization of Light Oil, Tokyo, Japan

[21] Appl. No.: 731,309

[22] Filed: Jul. 17, 1991

Related U.S. Application Data

[63] Continuation of Ser. No. 177,945, Apr. 5, 1988, abandoned.

[30] Foreign Application Priority Data

Apr. 8, 1987 [JP] Japan .................................. 62-84627

[51] Int. Cl.⁵ ......................... C12P 13/22; C12N 1/04; C12N 1/20
[52] U.S. Cl. ................................ 435/108; 435/252.9; 435/260; 435/849
[58] Field of Search ............ 435/108, 849, 260, 252.8

[56] References Cited

FOREIGN PATENT DOCUMENTS

| 045307 | 3/1980 | Japan | 435/108 |
| 134094 | 6/1987 | Japan | 435/108 |
| 883029 | 11/1981 | U.S.S.R. | 435/108 |

OTHER PUBLICATIONS

"Patent Abstracts of Japan", unexamined applications, C field, vol. 12, No. 391, Oct. 18, 1988, p. 83 C 537.
"Patent Abstracts of Japan", unexamined applications, C field, vol. 11, No. 365, Nov. 27, 1987, p. 1 C 460.

Primary Examiner—Irene Marx
Attorney, Agent, or Firm—Wenderoth, Lind & Ponack

[57] ABSTRACT

A method of selectively inhibiting pyruvic acid decomposition activity in microorganism cells containing tryptophanase or a treated product thereof, which comprises heat-treating said cells or the treated product thereof in the presence of an ammonium ion.

11 Claims, No Drawings

METHOD OF TREATING MICROORGANISM CELLS CONTAINING TRYPTOPHANASE OR TREATED PRODUCT THEREOF

This application is a continuation of now abandoned application, Ser. No. 07/177,945 filed Apr. 5, 1988.

This invention relates to a method of treating microorganism cells containing tryptophanase or a treated product thereof. More specifically, this invention relates to a method of selectively inhibiting the decomposition activity of pyruvic acid without substantially decreasing tryptophanase activity in microorganism cells containing tryptophanase or a treated product thereof.

It is known that L-tryptophan is produced by enzymatically reacting indole, pyruvic acid or its salts, and ammonium or an ammonium ion in the presence of microorganism cells containing tryptophanase or a treated product thereof [T. Watanabe and E. E. Snell, "Proceedings of National Academy of Science, U. S. A.", vol. 69, No. 5, pages 1086-1090 (1972)].

Pyruvic acid is one substance which participates in various metabolisms in animals and plants, and microorganism cells containing tryptophanase or a treated product thereof contains an enzyme which is involved in the metabolism of pyruvic acid in addition to tryptophanase. If, therefore, the microorganism cells containing tryptophanase or the treated product thereof is used in the production of L-tryptophan by enzymatic reaction, the starting pyruvic acid or its salt is used in the formation of L-tryptophan and also consumed by the decomposition reaction of pyruvic acid. Hence, the yield of the desired L-tryptophan decreases.

The freezing-thawing method and the heat-treatment method are generally known for the inhibition of enzyme activity. If these methods are applied to the microorganism cells containing tryptophanase or the treated product thereof, not only the pyruvic acid decomposition reaction but also the tryptophanase activity is inhibited. Accordingly, these methods cannot be used.

The present inventors made extensive investigations on a method of inhibiting the pyruvic acid decomposition activity of an enzyme participating in the metabolism of pyruvic acid without substantially reducing the tryptophanase activity in microorganism cells containing tryptophanase or the treated product thereof. These investigations have led to the discovery that when the microorganism cells containing tryptophanase or the treated product thereof is heat-treated in the presence of an ammonium ion, the pyruvic acid decomposition activity can be selectively inhibited without substantially reducing the tryptophanase activity.

According to this invention, there is provided a method of selectively inhibiting pyruvic acid decomposition activity in microorganism cells containing tryptophanase or a treated product thereof, which comprises heat-treating said microorganism cells or the treated product thereof in the presence of an ammonium ion.

If the microorganism cells or the treated product thereof, which is heat-treated by the method of this invention, is used for the production of L-tryptophan from indole, pyruvic acid or its salt and ammonia or an ammonium ion, the consumption of pyruvic acid by a side-reaction is inhibited, the conversion of pyruvic acid into L-tryptophan is effectively promoted, and the yield of L-tryptophan can be markedly increased.

The tryptophanase-containing cells used in the method of this invention include cells containing tryptophanase produced and accumulated sufficiently therein as a result of cultivating microorganisms having the ability to produce tryptophanase. Such microorganisms may be of any family or genus if they have the ability of producing tryptophanase. Specific examples are given below. It should be understood however that they are mere examples, and the scope of the invention is not limited thereto.

*Escherichia coli* ATCC 27325
*Escherichia coli* ATCC 25019
*Escherichia coli* IFO 3301
*Escherichia coli* K-12 YK3002 (FERM BP-1733)
*Escherichia coli* K-12 YK3003 (FERM BP-1734)
*Providencia rettgeri* ATCC 9250
*Proteus vulgaris* ATCC 6059
*Flavobacterium meningosepticum* ATCC 13253

These tryptophanase-producing microorganisms may be used in the method of this invention after they are cultured to accumulate tryptophanase sufficiently within their cells. Culturing of the microorganisms may generally be carried out by using ordinary synthetic or natural media containing carbon sources, nitrogen sources and inorganic substances. The carbon sources may be, for example, various carbohydrates such as glycose, glycerol, fructose, sucrose and molasses. The nitrogen sources include, for example, natural organic nitrogen sources such as tryptone, yeast extract, corn steep liquor, and casein hydrolyzate. Many of the natural organic nitrogen sources can also serve as carbon sources. Further examples of nitrogen sources are ammonium salts such as ammonium chloride, ammonium sulfate and ammonium phosphate, nitrates such as sodium nitrate, potassium nitrate and ammonium nitrate, and ammonia. Examples of the inorganic substances are potassium phosphate, magnesium sulfate, iron, manganese and zinc. Examples of the inorganic substances are potassium phosphate, magnesium sulfate, iron, manganese and zinc. As required, nutrients such as vitamins and amino acids may be added.

The culturing may be carried out under aerobic conditions by shaking culture, or submerged culture with aeration and agitation. The culturing temperature is generally 20° to 50° C., preferably 30° to 40° C. Desirably, the pH of the culture medium is usually 6 to 9, preferably 7 to 8. The culturing period is usually 1 to 5 days.

If an iron ion is continuously or intermittently added to the culture medium so that the iron ion concentration is maintained at not more than 0.15 mM, preferably 0.02 to 0.1 mM, the microorganism having a high tryptophanase activity can be obtained in a large quantity. As a source of the iron ion to be added to the medium, there may be used, for example, iron sulfate, iron chloride and iron nitrate. These salts may be added to the culture medium while the concentration of the iron ion is monitored in a conventional manner by, for example, colorimetry.

Microorganism cells having high tryptophanase activity can also be obtained in large quantities by continuously or intermittently adding an alkaline substance to the culture medium so as to maintain the pH of the culture medium at 7.0 to 7.4. The alkaline substance that can be used for pH control of the medium may be a substance which when added to the culture medium, causes the pH of the culture medium to shift to an alkaline side, and does not substantially exert a deleterious action on the microorganism in the culture medium. Examples may be ammonia, aqueous ammonia, alkalies and aqueous solutions of alkalies. Aqueous ammonia, aqueous solution of sodium hydroxide, an aqueous solution of potassium hydroxide and an aqueous solution of calcium hydroxide are preferred.

The tryptophanase-producing cells so cultured are harvested from the culture medium, and may be heat-treated by the method of this invention either directly or after the harvested microorganism cells are treated by physical means such as ultrasonication and squeezing to rupture the cell membranes; by chemical means using chemicals or enzymes to rupture the cell membranes; extracts obtained by extracting these ruptured products with water or another extractant; or a "treated product" of the above tryptophanase-containing cells obtained by treating the extracts with ammonium sulfate or the like to precipitate the enzyme component. Products obtained by immobilizing the above cells or the treated product thereof, by a known method, for example the method described in "Methods in Enzymology", vol. 44 (1977), edited by K. Moskauch, may be used as the "treated product" of the cells in the method of this invention.

According to the method of this invention, the tryptophanase-containing cells or the treated product thereof is heat-treated in the presence of an ammonium ion. This heat-treatment may be carried out by suspending the cells or the treated product thereof in an aqueous medium and adding an ammonium ion source. The ammonium ion source that can be added may be any of ammonium-containing compounds which dissolve in water to liberate an ammonium ion and do not contain components that substantially adversely affect the tryptophanase activity. Examples of preferred ammonium-containing compounds are ammonium chloride, ammonium sulfate and ammonium phosphate. Ammonium nitrate should not be used because it inhibits tryptophanase.

The concentration of the ammonium ion in the aqueous medium is not strictly limited, and may be varied over a wide range according to the type of the cells or the treated product thereof, and the degree of treatment. Generally, it is 100 to 10,000 mg/liter, preferably 500 to 8,000 mg/liter, especially preferably 1,000 to 5,000 mg/liter, as the ammonium ($NH_4$) ion. The pH of the aqueous medium used in the heat-treatment is generally 5 to 9, preferably 6 to 8, more preferably 7 to 8.

Water or a buffer solution such as potassium phosphate buffer or tris-hydrochloric buffer may be generally used as the aqueous medium. If desired, a minor proportion of a water-miscible surface-active agent, preferably a nonionic surface-active agent such as Triton X-100, Tween 20 and Tween 40, may be added to the medium.

The concentration of the cells or the treated product thereof in the aqueous medium is neither critical, and may be varied widely depending upon the concentration of the ammonium ion. Generally, it is 0.1 to 50 % (wt/vol), preferably 0.5 to 30 % (wt/vol), more preferably 1 to 20 % (wt/vol). When the concentration of the cells or the treated product thereof is high, the concentration of the ammonium ion is desirably higher within the above range. Any one skilled in the art would be able to determine the optimum combination of these concentrations by performing a small-scale routine experiment.

The heat-treating temperature in accordance with this invention is generally 40° to 80° C., preferably 50° to 70° C., especially preferably 55° to 60° C. At this temperature, the heat-treatment may be carried out usually for 2 minutes to 24 hours, preferably about 5 minutes to 6 hours.

The tryptophanase-containing cells or the treated product thereof, which has been heat-treated as above by the method of this invention, has markedly inhibited pyruvic acid decomposition activity without a substantial reduction in tryptophanase activity, and can advantageously be used as an enzyme catalyst in the production of L-tryptophan by the reaction of indole, pyruvic acid or its salt and ammonia or an ammonium ion, as will be demonstrated by examples given below.

The reaction of synthesizing L-tryptophan can be carried out in quite the same way as in known L-tryptophan-synthesizing reactions except that the tryptophanase-containing cells or the treated product thereof, which is heat-treated by the method of the invention, is used. For example, it is carried out in a solvent such as 0.1 M phosphate buffer (pH 7.5-10.0) or water (pH 7.5-10.0) at a temperature of about 20° to 50° C., preferably about 30° to 40° C., for a period of usually about 2 to 72 hours.

There is no particular restriction on the amounts of indole, pyruvic acid or its salt (such as an alkali metal pyruvate), and ammonium or an ammonium ion (an ammonium salt of an organic acid such as ammonium acetate may also be used besides the above-mentioned ammonium ion sources) used in the reaction so long as they are used in concentrations which do not inhibit the enzymatic reaction. Generally, the suitable concentration of each of these materials is in the range of 0.1 to 20% (wt/vol), preferably 0.5 to 10% (wt/vol). The ratio of indole/pyruvic acid or its salt/ammonia or the ammonium ion is neither restricted strictly. Generally, the mole ratio of these is suitably 1:1-100:1-300, preferably 1:5-50:5-100.

The amount of the cells or the product thereof is not particularly restricted. Generally, they may be used in a concentration of 0.5 to 10% (wt/vol), preferably 0.8 to 8% (wt/vol).

Isolation of L-tryptophan from the reaction mixture after the reaction and its purification may be carried out by known methods, for example, adsorption and desorption on and from ion exchange resins and activated carbon.

The following Examples illustrate the present invention in greater detail.

EXAMPLE 1

One hundred milliliters of a an L-medium composed of 10 g of tryptone, 5 g of yeast extract, 5 g of sodium chloride, 1 g of glucose and 1 liter of distilled water (pH 7.2) was put in a 500 ml Erlenmeyer flask, and sterilized at 120° C. for 15 minutes. *Escherichia coli* K-12 YK3003 (FERM BP-1733), a tryptophanase-producing microorganism, was inoculated in the L-medium, and cultured at 37° C. for 1 day under shaking. Then, 20 ml of the culture broth was inoculated in 1,000 ml of L-medium containing L-tryptophan in a concentration of 200μg/ml (sterilized at 120° C. for 15 minutes) and cultured at 37° C. under shaking. The cells were harvested by centrifugation (6000 rpm, 15 minutes, 4° C.) from 100 ml of the resulting culture broth. The harvested cells were suspended in 10 ml of distilled water containing 5 % by weight of ammonium sulfate. The cell suspension was heat-treated for each of the periods of time indicated in Table 1, and then pyruvic acid decomposition activity and tryptophanase activity were measured.

The pyruvic acid decomposition activity was measured by the following procedure. All the treated cells were added to 25 ml of a reaction solution composed of 200 μmole of sodium pyruvate, 0.04 μmole of pyridoxalphosphoric acid, 100 μmole of NH4Cl, and distilled water to make 1 ml (pH 8.7 adjusted with 5N sodium hydroxide) and reacted at 37° C. for 24 hours. The amount of pyruvic acid was measured by liquid chromatography.

The tryptophanase activity was measured by the following procedure.

0.1 ml of the aforesaid treated cell suspension was added to 25 ml of a reaction solution which contained per ml thereof, 100μmole of phosphate buffer (pH 8.0), 5 μmole of L-tryptophan and 0.04μmole of pyridoxalphosphoric acid, and reacted at 37° C. for 15 minutes. The amount of indole formed was determined by a conventional method [O. H. Smith and C. Janofsky: "Methods in Enzymology", Academic, New York, (1962, vol. 5, pages 794–806)].

The pyruvic acid decomposition activity and the tryptophanase activity are shown in Table 1 as relative activities which were obtained by taking the enzyme activity before heat-treatment as 100.

TABLE 1

| Treating conditions | | Pyruvic acid decomposition activity (%) | Tryptophanase activity (%) |
|---|---|---|---|
| Temperature (°C.) | Time (min.) | | |
| — | 0 (before heat-treatment) | 100 | 100 |
| 45 | 60 | 50 | 99 |
| | 90 | 42 | 99 |
| 50 | 30 | 35 | 99 |
| | 60 | 26 | 98 |
| 55 | 15 | 21 | 95 |
| | 30 | 10 | 94 |
| 60 | 10 | 9 | 91 |
| | 20 | 7 | 86 |
| 65 | 5 | 9 | 88 |
| | 10 | 8 | 70 |
| | 20 | 6 | 62 |
| 70 | 5 | 5 | 41 |

EXAMPLE 2

The same microorganism as used in Example 1 was cultured under shaking as in Example 1, and further cultured under shaking in L-medium containing L-tryptophan. 25 ml of the resulting culture broth was centrifuged (6000 rpm, 15 minutes, 4° C.) to harvest the cells. The resulting cells were washed once with 20 ml of 100 mM Tris-HCl buffer (pH 7.5) and suspended in 1 ml of the same buffer. The cell suspension was subjected to rupturing by a cell rupturing device (Branson S-200). The ruptured product was centrifuged (12000 rpm, 40 minutes, 4° C.) to separate it into a supernatant and a precipitate.

Ammonium sulfate was added to 1 ml of the above supernatant (cell-free extract), and the concentration of ammonium sulfate was adjusted to 5 % by weight. The solution was heat-treated for each of the periods of time indicated in Table 2. The pyruvic acid decomposition activity and the tryptophanase activity were measured.

The pyruvic acid decomposition activity was measured by the following procedure. 0.1 ml of the heat-treated product was added to 1 ml of a reaction solution composed of 200 μmoles of sodium pyruvate, 0.04 μmole of pyridoxalphosphoric acid, 100 μmole of NH4Cl and distilled water to make 1 ml (pH 80 adjusted with 5N sodium hydroxide) and reacted at 37° C. for 24 hours. The amount of the remaining pyruvic acid was measured by liquid chromatography.

The tryptophanase activity was measured by the following procedure. 0.1 ml of a diluted solution of the heat-treated product (diluted to 100-fold with 100 mM Tris-HCl buffer, pH 8.0) was added to 1 ml of a reaction solution containing 100 μmole of phosphate buffer (pH 8.0), 5 μmole of L-tryptophan and 0.04 μmole of pyridoxalphosphoric acid, and reacted at 37° C. for 15 minutes. Thereafter, the tryptophanase activity was measured by the same method as in Example 1.

The results are shown by relative activity values as in Example 1 in Tale 2.

TABLE 2

| Treating conditions | | Pyruvic acid decomposition activity (%) | Tryptophanase activity (%) |
|---|---|---|---|
| Temperature (°C.) | Time (min.) | | |
| — | 0 (before heat-treatment) | 100 | 100 |
| 40 | 60 | 62 | 98 |
| | 90 | 48 | 98 |
| 50 | 20 | 28 | 98 |
| | 30 | 15 | 97 |
| 55 | 10 | 6 | 97 |
| | 20 | 3 | 95 |
| 60 | 5 | 3 | 91 |
| | 10 | 2 | 84 |

EXAMPLE 3

Example 1 was repeated except that in the heat-treatment, the temperature was changed to 60° C. and the time, to 10 minutes, and the concentration of the ammonium ion was changed as shown in Table 3. The results are shown in Table 3.

TABLE 3

| Concentration of the ammonium ion added (wt %) | Tryptophanase activity (%) | Pyruvic acid decomposition activity (%) |
|---|---|---|
| as (NH4)2SO4 | | |
| 0 | 45 | 45 |
| 0.1 | 68 | 20 |
| 0.5 | 75 | 16 |
| 1 | 88 | 12 |
| 5 | 91 | 9 |
| 10 | 91 | 9 |
| 20 | 92 | 8 |
| as NH4Cl | | |
| 0 | 45 | 45 |
| 0.2 | 73 | 15 |
| 0.4 | 87 | 10 |
| 4 | 90 | 9 |
| 8 | 91 | 9 |
| as (NH4)3PO4 | | |
| 0 | 45 | 46 |
| 0.15 | 69 | 22 |
| 1.5 | 87 | 11 |
| 15 | 90 | 8 |

EXAMPLE 4

Example 2 was repeated except that in the heat-treatment, the temperature was changed to 55° C. and the time, to 10 minutes, and the concentration of the ammonium ion was changed as shown in Table 4. The results are shown in Table 4.

TABLE 4

| Concentration of the ammonium ion added (wt %) | Tryptophanase activity (%) | Pyruvic acid decomposition activity (%) |
| --- | --- | --- |
| as $(NH_4)_2SO_4$ | | |
| 0 | 43 | 40 |
| 0.1 | 75 | 14 |
| 0.5 | 90 | 8 |
| 1 | 94 | 8 |
| 5 | 97 | 6 |
| 10 | 97 | 6 |
| 20 | 97 | 6 |
| as $NH_4Cl$ | | |
| 0 | 44 | 39 |
| 0.2 | 91 | 7 |
| 0.4 | 93 | 7 |
| 4 | 96 | 6 |
| 8 | 97 | 6 |
| as $(NH_4)_3PO_4$ | | |
| 0 | 43 | 40 |
| 0.15 | 74 | 15 |
| 1.5 | 94 | 8 |
| 15 | 97 | 6 |

EXAMPLE 5

1000 ml of a culture broth prepared in the same way as in Example 1 was centrifuged (6000 rpm, 15 minutes, 4° C.) to harvest the cells. The cells were suspended in 100 ml of distilled water containing 50 mg/ml of ammonium sulfate. The cell suspension was heat-treated in a constant-temperature vessel at 60° C. for 10 minutes with shaking, and then centrifuged (6000 rpm, 15 minutes, 4° C.) to harvest the cells. The cells were then suspended in 50 ml of 100 mM Tris-Hcl buffer containing 0.25 g of indole, 0.25 g of sodium pyruvate, 0.5 g of ammonium acetate, 0.5 mg of pyridoxalphosphoric acid and 0.5 g of KCl, and with shaking, these compounds were reacted at 37° C. for 3 hours. After the reaction, the reaction mixture was diluted to 10-fold with water, and centrifuged. The supernatant was analyzed for L-tryptophan by high-performance liquid chromatography. The formation of 0.62 m9/ml of L-tryptophan was determined. After the reaction, 500 ml of the aforesaid 10-fold dilution was passed through a column of strong acid type ion-exchange resin (ammonia type; "DIAION® SK-1B", a product of Mitsubishi Chemical Co., Ltd.). The column was eluted with an alkaline solution, and the eluate was concentrated to precipitate crude crystals of L-tryptophan. The crude crystals were washed with acetone and dried to give 205 mg of crystals of L-tryptophan.

When the above reaction was repeated using the aforesaid cells without heat-treatment, the amount of L-tryptophan formed was 0.41 mg/ml.

EXAMPLE 6

Example 5 was repeated except that *Escherichia coli* K-12 YK3003 (FERM BP-1734) was used instead of the microorganism used in Example 5. L-tryptophan formed in an amount of 0.63 mg/ml when the heat-treated cells were used, and in an amount of 0.39 mg/ml when the non-heat-treated cells were used.

The amount of L-tryptophan crystals recovered from 50 ml of the reaction mixture obtained by the reaction carried out by using the heat-treated cells was 208 mg.

What we claim is:

1. A method of selectively inhibiting pyruvic acid decomposition activity in *Escherichia coli* selected from the group consisting of *Escherichia coli* K-12 YK3002, *Escherichia coli* YK3003, *Escherichia coli* ATCC 27325, *Escherichia coli* ATCC 25019 and *Escherichia coli* IFO 3301, which comprises heat-treating said *Escherichia coli* at a temperature of 50° to 70° C. in the presence of ammonium ion of a concentration of 100 to 10,000 mg/liter.

2. The method of claim 1 wherein ammonium chloride, ammonium sulfate or ammonium phosphate is used as a source of the ammonium ion.

3. The method of claim 1 wherein the heat-treatment is carried out in an aqueous medium.

4. The method of claim 1 wherein the concentration of the ammonium ion is 500 to 8,000 mg/liter.

5. The method of claim 3 wherein the pH of the aqueous medium at the time of the heat-treatment is 5 to 9.

6. The method of claim 5 wherein the pH of the aqueous medium at the time of the heat-treatment is 6 to 8.

7. The method of claim 3 wherein the concentration of the cells or the treated product thereof in the aqueous medium is 0.1 to 50% (wt/vol).

8. The method of claim 1 in which the heat treatment is carried out at a temperature of 55° to 60° C.

9. The method of claim 1 wherein said *Escherichia coli* is in the form of (1) cells of said *Escherichia coli*, (2) ruptured cells of said *Escherichia coli*, (3) cell free extracts of said *Escherichia coli* or (4) immobilized preparation thereof.

10. A method of producing L-tryptophan by reacting indole, pyruvic acid or its salt, and ammonia or ammonium ion in the presence of *Escherichia coli* selected from the group consisting of *Escherichia coli* K-12 YK-3002, *Escherichia coli* K-12 YK3003, *Escherichia coli* ATCC 27325, *Escherichia coli* ATCC 25019 and *Escherichia coli* IFO 3301, and harvesting L-tryptophan from the reaction mixture, wherein said *Escherichia coli* has been subjected to heat-treatment at a temperature of 50° to 70° C. in the presence of ammonium ion at a concentration of 100 to 10,000 mg/liter.

11. The method of claim 10 wherein said *Escherichia coli* is in the form of (1) cells of said *Escherichia coli*, (2) ruptured cells of said *Escherichia coli*, (3) cell free extracts of said *Escherichia coli* or (4) immobilized preparation thereof.

* * * * *